(12) United States Patent
Steen

(10) Patent No.: US 10,271,540 B2
(45) Date of Patent: Apr. 30, 2019

(54) MEDICAL FLUID, A METHOD OF TREATMENT AND USE OF THE FLUID

(71) Applicant: XVIVO PERFUSION AB, Göteborg (SE)

(72) Inventor: Stig Steen, Lund (SE)

(73) Assignee: XVIVO PERFUSION AB, Göteborg (SE)

( * ) Notice: Subject to any disclaimer, the term of this patent is extended or adjusted under 35 U.S.C. 154(b) by 143 days.

(21) Appl. No.: 15/229,356

(22) Filed: Aug. 5, 2016

(65) Prior Publication Data

US 2016/0338343 A1 Nov. 24, 2016

Related U.S. Application Data

(63) Continuation of application No. 13/697,839, filed as application No. PCT/SE2011/000083 on May 13, 2011, now abandoned.

(60) Provisional application No. 61/396,709, filed on Jun. 2, 2010.

(30) Foreign Application Priority Data

May 14, 2010 (SE) ...................................... 1000518

(51) Int. Cl.
*A01N 1/02* (2006.01)
(52) U.S. Cl.
CPC ................................. *A01N 1/0226* (2013.01)
(58) Field of Classification Search
None
See application file for complete search history.

(56) References Cited

U.S. PATENT DOCUMENTS

| | | | |
|---|---|---|---|
| 6,432,401 | B2 | 8/2002 | Weber et al. |
| 8,012,677 | B2 | 9/2011 | Steen |
| 2006/0166360 | A1 | 7/2006 | Berthiaume et al. |
| 2006/0253075 | A1 | 11/2006 | Faries et al. |
| 2006/0292544 | A1 * | 12/2006 | Hassanein .............. A01N 1/02 435/2 |
| 2008/0176205 | A1 * | 7/2008 | Shelby ................... A01N 1/02 435/1.1 |
| 2010/0074897 | A1 | 3/2010 | Huang |
| 2011/0270215 | A1 | 11/2011 | Steen |
| 2013/0065218 | A1 | 3/2013 | Steen |

FOREIGN PATENT DOCUMENTS

| | | | | |
|---|---|---|---|---|
| WO | 0185171 | A1 | 11/2001 | |
| WO | 0235929 | A1 | 5/2002 | |
| WO | 2004034887 | A2 | 4/2004 | |
| WO | WO-2004034887 | A2 * | 4/2004 | ............... A01N 1/02 |
| WO | 2010077200 | A1 | 7/2010 | |
| WO | 2010077201 | A1 | 7/2010 | |

OTHER PUBLICATIONS

Oxford English Dictionary, Definition of "denervated", available online at <<https://en.oxforddictionaries.com/definition/denervated>> , copy right 2018 (Year: 2018).*
Schnuelle et al. "Donor cetcholamine use reduces acture allograft rejection and imporves graft survival after cadaveric real transplantation", Kidney International 56: 738-746, 1999 (Year: 1999).*
Muir et al. "Cocaine potentiates the blood pressure and cerebral blood flow response to norepinephrine in rats", European Journal of Pharmacology, 249: 287-292, 1993 (Year: 1993).*
European Search Report dated Jun. 13, 2012 in EP Appn. No. 09836460.7, 8 pages.
International Search Report for PCT/SE2009/000542, dated Apr. 7, 2010.
International Search Report for PCT/SE2009/000541 dated Apr. 7, 2010.
European Search Report dated Nov. 13, 2013 in EP Appn. No. 11780879, 13 pages.
Iversen, "The Uptake of Noradrenaline by the Isolated Perfused Rat Heart," Brit. J. Phamacol. (1963), vol. 21, pp. 523-537.
McCorry, "Physiology of the Autonomic Nervous System," American Journal of Pharmaceutical Education (2007), vol. 71, pp. 1-11.
Sasaki, et al. "Impact of Initial Flush Potassium Concentration on the Adequacy of Lung Preservation," J. Thorac. Cardiovasc. Surg. (1995), vol. 109, pp. 1090-1096.
Schwartz, et al., "Cardiovascular Effects of Cocaine," Circulation (2010), vol. 122, pp. 2558-2569.
Shemie, et al., "Organ donor management in Canada: Recommendations of the forum on medical management to optimize donor organ potential," CMAJ vol. 174, No. 6, pp. S13-530, Mar. 14, 2006.
International Search Report for PCT/SE2011/000083 dated Aug. 29, 2011.
Bohm, et al., "Evidence for Reduction of Norepinephrine Uptake Sites in the Failing Human Heart," JACC, vol. 25, No. 1, Jan. 1995, pp. 146-153.
Muir, et al., "Cocaine potentiates the blood pressure and cerebral blood flow response to norepinephrine in rats," European Journal of Pharmacology, vol. 29, 1993, pp. 287-292.

(Continued)

*Primary Examiner* — Emily A Cordas
(74) *Attorney, Agent, or Firm* — Pearne & Gordon LLP

(57) ABSTRACT

A medical fluid for a harvested organ, tissue or part thereof, for evaluation and/or preservation. The fluid includes cocaine or a stimulating analog thereof; noradrenaline; and/or adrenaline. In addition, the fluid includes an oncotic agent, such as dextran; hormones, such as thyroxin; triiodotyronine; cortisone, insulin; and electrolytes and optionally nutrients in substantially physiological concentrations in a physiologically acceptable medium. In addition, the medical fluid further includes albumin in a concentration not exceeding 5.0%, and an oxygen carrier, such as erythrocytes. Further components may be dopamine; hydrocortisone; methylprednisolone; and a vasopressor agent, such as desmopressin. The cocaine; adrenaline; and noradrenaline are present in concentrations of each about 0.010 μM to 0.100 μM, for example in a ratio of 1:1:1.

16 Claims, 1 Drawing Sheet

(56) References Cited

OTHER PUBLICATIONS

Schnuelle, et al., "Donor catecholamine use reduces acute allograft rejection and improves graft survival after adaveric renal transplantation," Kidney International, vol. 56, 1999, pp. 738-746.

Wijnen, et al., "Donor treatment after pronouncement of brain death: a neglected intensive care problem," Transplant International, vol. 4, 1991, pp. 186-190.

Bentley, "The effect of local anaesthetic and anti-adrenaline drugs on the response of sympathetically innervated smooth muscle preparations to electrical stimulation at different frequencies," British journal of Pharmacology and Chemotherapy, vol. 27, 1966, pp. 64-80.

Easton, et al., "Effects of amphetamine isomers, methylphenidate and atomoxetine on synaptosomal and synaptic vesicle accumulation and release of dopamine and noradrenaline in vitro in the rat brain," Neuropharmacology, vol. 52, 2007 pp. 405-414.

John, "Donor management and selection for heart transplantation," Seminars in Thoracic and Cardiovascular surgery. vol. 16, 2004, pp. 364-369.

Johnsson, et al., "Interaction studies between three antidepressant drugs (chlorimipramine, imipramine and zimelidine) and noradrenaline, tyramine and vagal stimulation on the heart rate and blood pressure in dogs," Acta Pharmacologica et Toxicologica vol. 45, 1979, pp. 192-197.

Kucheruk, "Effect of noradrenalin on duration of local anesthesia," Bulletin of Experimental Biology and Medicine vol. 54, 1962, pp. 761-762.

Kurth, et al., "Cocaine and its metabolites constrict cerebral arterioles in newborn pigs," Journal of Pharmacology and Experimental Therapeutics, vol. 265, 1993, pp. 587-591.

Lange, et al., "The effect of nasal application of cocaine/adrenaline on blood loss in Le Fort I osteotomies," International Journal of Oral and Maxillofacial Surger, vol. 37, 2008, pp. 21-24.

Pradhan, et al., "Effect of acute intravenous cocaine administration on endothelium-dependent vasodepressor responses to acetylcholine," Journal of Cardiovascular Pharmacology and Therapeutic, vol. 8, 2003, pp. 43-51.

Schulak, et al., "Donor pretreatment with lidocaine decreases incidence of early renal dysfunction in cadaver kidney ransplantation," Transplantation Proceedings. vol. 22, 1990, pp. 353-354.

Sun, et al. "Low-dose vasopressin in the treatment of septic shock in sheep," American Journal of Respiratory and Critical Care Medicine, vol. 168, 2003, pp. 481-486.

Wood, at al., "Management of the potential organ donor," Transplantation Reviews, vol. 21, 2007, pp. 204-218.

Zaky, et al. "Hemodynamic and metabolic efficacy of dopamine versus norepinephrine in a brain-dead swine model." Liver Transplantation, vol. 14, 2008, pp. 1266-1272.

Johnson, et al., "Local Anesthetics as Antimicrobial Agents: A Review", Surgical Infections, vol. 9, No. 2, 2008, pp. 205-213.

The Merck Index, Twelfth Edition, Abstracts 2517 (pp. 415-416), 7991 (p. 1342), and 9330 (p. 1570, including enlarged view of abstract), published by Merck Research Laboratories, 1996, pp. 1-7 in PDF.

* cited by examiner

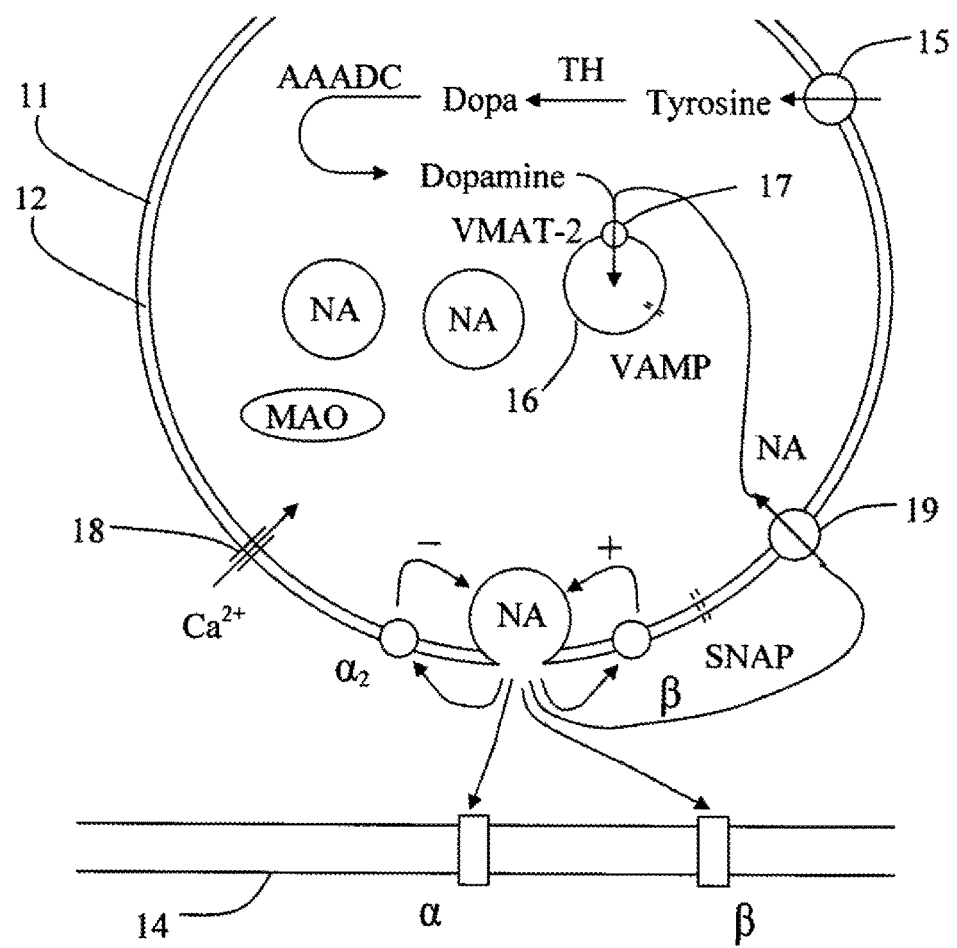

MEDICAL FLUID, A METHOD OF TREATMENT AND USE OF THE FLUID

CROSS-REFERENCE TO RELATED APPLICATIONS

This application is a continuation of U.S. application Ser. No. 13/697,839, filed Nov. 14, 2012, which is a national stage application of International Appl. PCT/SE2011/000083, filed May 13, 2011, which claims the benefit of provisional U.S. Application No. 61/396,709, filed Jun. 2, 2010, and which claims priority of Swedish Patent Appl. No. 1000518-9, filed May 14, 2010, all of which are hereby incorporated by reference.

FIELD OF INVENTION

The present invention relates to a method of handling an organ after harvesting, including a medical fluid and use of said fluid.

BACKGROUND OF THE INVENTION

It is well known that there is a great shortage of donor organs, which may be used for transplantation.

After harvesting, the organs should be examined and evaluated for viability to be used for transplantation purpose. The evaluation may be performed at a physiological temperature of about 37° C., such as between 30° C. and 40° C., or alternatively at a lower temperature. During the evaluation, the organs may be perfused by and/or surrounded by an evaluation fluid similar to blood.

Normally, the organs cannot be transplanted immediately, but a recipient should be found, which may take some time. Moreover, the organ to be transplanted should be transported to the recipient or the recipient be transported to the organ. Thus, the organs may be preserved for some hours or days, often at hypothermal conditions. During preservation, the organs may be perfused by and/or surrounded by a preservation fluid.

There are several previously known evaluation fluids and preservation fluids. Such medical fluids involve compromises between cost and performance.

An evaluation fluid may operate at a physiological temperature of about 37° C. and provide support for metabolism of the organ, at least to a certain degree. Such a fluid may be whole blood or a synthetic fluid operating similar to blood, or a combination.

A preservation fluid may be optimized for operation at low temperature, during which the metabolism of the organ is low.

There is a need for a medical fluid, which is more versatile than those presently used, and which is suitable for evaluation and preservation of organs after harvesting and before transplantation.

WO2010077200A1 and WO2010077201A1 disclose fluids which are used for supporting body functions in a brain-dead body. The contents of these patent applications are incorporated in the present specification by reference.

DISCLOSURE OF THE INVENTION

Accordingly, an object of the present invention is to mitigate, alleviate or eliminate one or more of the above-identified deficiencies and disadvantages singly or in any combination.

In an aspect, there is provided a medical fluid for a harvested organ, tissue or part thereof, for evaluation and/or preservation, comprising: cocaine or a stimulating analogue thereof; adrenaline (also termed adrenalin) and/or noradrenaline (also termed noradrenalin); an oncotic agent; hormones; and electrolytes and optionally nutrients in substantially physiological concentrations in a physiologically acceptable medium. Cocaine, noradrenaline, if present, and adrenaline, if present, may be in concentrations of about 0.010 µM to 0.100 µM. The oncotic agent may be albumin or dextran or a combination thereof. The hormones may be any one of thyroxin; triiodotyronine; or cortisone or a combination thereof. The fluid may further comprise an oxygen carrier, such as erythrocytes. The fluid may further comprise at least one of glucose; insulin; dopamine; hydrocortisone; methylprednisolone; and a vasopressor agent, such as desmopressin. The cocaine or a stimulating analogue thereof; adrenaline; and noradrenaline may be present in concentration ratios of 1:1:1.

In another aspect, there is provided a method for treatment of a harvested organ for evaluation and/or preservation, comprising: circulating a first fluid in the vascular system of the organ, and optionally partly or completely immersing said organ in a second fluid; said first fluid comprising cocaine or a stimulating analogue thereof; adrenaline and/or noradrenaline; an oncotic agent; hormones; and electrolytes and optionally nutrients in substantially physiological concentrations in a physiologically acceptable medium.

In a further aspect, there is provided a use of a fluid for a harvested organ, tissue or part thereof for evaluation and/or preservation, wherein the fluid comprises the components mentioned above.

BRIEF DESCRIPTION OF THE DRAWINGS

Further objects, features and advantages of the invention will become apparent from the following detailed description of embodiments of the invention with reference to the drawings, in which FIG. 1 is a schematic view of a nerve terminal.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

Definitions

In the context of the present description and embodiments the following definitions apply: The term "cocaine analogue" is intended to mean an analogue, which acts in the same or a similar way as cocaine in preserving organs after harvesting of the organs. The term "pharmaceutically acceptable" means a non-toxic material that does not decrease the effectiveness of the biological activity of the active ingredients. The term "physiologically acceptable solution" means a solution that does not interfere substantially with the fluids in the body. Such pharmaceutically acceptable buffers, carriers or excipients are well-known in the art, see for example Remington's Pharmaceutical Sciences, 18th edition, A. R. Gennaro, Ed., Mack Publishing Company (1990) and handbook of Pharmaceutical Excipients, 3rd edition, A. Kibbe, Ed., Pharmaceutical Press (2000).

An object of the below described embodiments is to improve the outcome of organs harvested from a donor and transplanted to a recipient. A hypothesis is that the outcome of organs after transplantation may be improved by use of a fluid comprising adrenaline (epinephrine) and/or noradrenaline (norepinephrine). Thus, an understanding of the role of these catecholamines in the living human and/or mammalian body is of interest.

Adrenaline and noradrenaline are neurotransmitters which influence upon alpha- and beta-receptors, and have numerous actions in the body.

Adrenaline and noradrenaline may as well be regarded as hormones because they are secreted by the adrenal medulla into the blood stream in the living (mammal) body. Normal human secretion in the adrenal medulla of adrenaline may be 0.2 μg per kg and min and of noradrenaline 0.05 μg per kg and min. Normal plasma adrenaline concentration is about 0.05 to 0.5 mg per liter in a living human body. In certain conditions, the plasma adrenaline concentrations may be increased more than ten times.

In addition, noradrenaline is produced in the pre-synaptic adrenergic nerve terminal from tyrosine, which is an amino acid present all over the body in large quantities.

FIG. 1 is a schematic and simplified view showing a nerve terminal of the sympathetic nerve system. The nerve terminal ends in a presynaptic adrenergic varicosity 11 having a cell membrane 12. A postsynaptic effector cell membrane 14 is positioned a short distance from the cell membrane 12. The distance is called the synaptic cleft and may be about 20 nm in a chemical synapse.

Tyrosine is transported into the varicosity 11 via a transporter 15 and into the cytoplasm, wherein the tyrosine is converted to DOPA under the influence of an enzyme; tyrosine hydroxylase (TH). This step is considered to be the rate-limiting step in the synthesis of noradrenaline and adrenaline.

DOPA is transformed to dopamine in the cytoplasm under the influence of an enzyme; aromatic L-amino acid decarboxylase (AAADC).

Dopamine is taken up into vesicles 16 via an active transporter 17 called VMAT-2 (vesicular monoamine transporter), which is relatively non-specific and can transport different catecholamines, such as noradrenaline and dopamine, and other substances. Only about 50% of the dopamine produced is normally transported into the vesicles 16; the rest is metabolized in the cell by an enzyme called MAO (monoamine oxidase), see further below. There are a great number of vesicles in the nerve terminal.

Inside the vesicle, there is an enzyme; dopamine-β-hydroxylase (DβH), which converts the dopamine entering the vesicle into noradrenaline (NA). In addition, any noradrenaline present inside the varicosity 11 is transported into the vesicle 16 by the same transporter 17, VMAT-2. In this way, noradrenaline is reused. A portion of the noradrenaline inside the varicosity does not enter the vesicle 16 but is metabolized by the enzyme MAO. Thus, there is a competition between the enzyme MAO and the active transporter 17 VMAT-2, both with regard to dopamine and noradrenaline.

The concentration of noradrenaline inside the vesicle is very high. A concentration in the range of 1 mole/liter has been reported.

At depolarization of the nerve cell membrane at the arrival of a stimulation signal, several voltage dependent calcium ion channels 18 allow the passage of calcium ions through the varicosity membrane 12. Elevated levels of calcium ions promote the fusion of vesicular membrane with the membrane of the varicosity with subsequent exocytosis of noradrenaline, NA. The fusion process involves the interaction of specialized proteins associated with the vesicular membrane (VAMPs, vesicle-associated membrane proteins) and the membrane of the varicosity (SNAPs, synaptiosome-associated proteins). When the vesicle emits its content into the synaptic cleft, the noradrenaline passes into the synaptic cleft and may interact with alpha- and beta-receptors present at the effector cell membrane, as shown by arrows in FIG. 1. Since the concentration of noradrenaline in the vesicle is extremely high and because the concentration of noradrenaline in the synaptic cleft normally is very low, and because the distance across the synaptic cleft is very small, some 20 nm, the noradrenaline will more or less explode when released from the vesicle due to the high concentration gradient and rapidly reaches the receptors at the effector cell membrane. The entire process comprising receipt of a depolarization voltage, inflow of calcium and exocytosis of noradrenaline takes often less than one tenth of a second.

The released noradrenaline may also interact with pre-synaptic receptors of alpha-2-type and beta-type. The alpha-2-receptor may influence directly on the vesicle and diminish the release of noradrenaline. The beta-receptor may facilitate the release of noradrenaline. The mechanism is not clearly understood for such direct influence of the release of the noradrenaline.

After some time, noradrenaline attached to the receptors is released from the receptors in the synaptic cleft. The noradrenaline present in the synaptic cleft is transported into the adrenal varicosity by an active transporter 19, called NET (norepinephrine transporter, norepinephrine=noradrenaline). This transporter has a high affinity for noradrenaline. NET removes free noradrenaline from the synaptic cleft, often within 0.1 seconds. However, a small portion of the free noradrenaline in the synaptic cleft passes out to the surrounding interstitial fluid and subsequently to the vascular blood circulation. Circulating noradrenaline is rapidly metabolized in the liver, normally within a few minutes.

Thus, most of the noradrenaline released during exocytosis is reused. A portion is lost to the circulation and a portion is lost inside the adrenergic varicosity due to metabolization by MAO before entering the vesicle 16. Such lost noradrenaline is replaced by newly produced noradrenaline from tyrosine as explained above.

There is a negative feed-back regulation of the synthesis of noradrenaline from tyrosine. Thus, a high concentration of noradrenaline at the presynaptic alpha-2-receptors seems to decrease the production of noradrenaline, probably via interference with the rate limiting enzyme TH.

The distance from the synaptic cleft to the blood circulation may be in the range of about 0.1 μm to several millimeters and is thus larger than the synaptic cleft. Thus, it takes a long time for noradrenaline to diffuse from the synaptic cleft to the blood circulation and vice versa. Consequently, the concentration of circulating noradrenaline in the blood of a living human body is normally low. In addition, it takes a high concentration in the blood in order for some noradrenaline to diffuse to the synaptic cleft and influence upon the receptors of the effector cell.

There are indications in the literature that a noradrenaline plasma concentration in the living body of about 1.5 mg per liter (about 9 μM) is required in order to observe a physiological change. The corresponding plasma concentration for adrenaline is about 0.05 mg per liter (0.3 μM).

Adrenaline is produced from noradrenaline by an extra enzymatically driven step in the adrenal medulla. The enzyme is called phenylethanolamine N-methyltransferase (PNMT) and converts noradrenaline to adrenaline. This enzyme is present essentially only in the adrenal medulla. The adrenal medulla comprises nerve terminals similar to the adrenergic varicosity shown in FIG. 1 but lacks a postsynaptic portion. Instead, the exocytosis takes place directly into the blood stream. Normally, the adrenal medulla excretes about 80% adrenaline and 20% noradrenaline into the blood.

The above description is valid for a living mammal body, such as the human body.

Circulating adrenaline and noradrenaline are metabolized by the liver and have a half-life of approximately a few minutes when circulating in blood. Other metabolization paths are also known.

It is reported in the literature that administration of noradrenaline to the vascular system has been associated with myocardial damage and initial nonfunctioning after cardiac transplantation. It is hypothesized that the noradrenaline may cause myocardial ischemia and/or desensitization of the beta-adrenergic signaling pathway. Administration of noradrenaline may further desensitize the myocardial beta-adrenergic signaling. The recovery potential of BAR remains unknown, but may have an impact on organ function.

When an organ has been harvested, the organ may be evaluated for suitability for transplantation. Such evaluation may involve administration of a medical fluid to the vascular system of the organ during physiological temperature.

If the organ is the heart, the evaluation may involve measurement of the organs ability to pump fluid. If the organ is the lungs, the organs ability to add oxygen and remove carbon dioxide may be measured. For other organs, the organs ability to operate as required may be assessed.

A medical fluid used for such purpose may be for example Steen Solution disclosed in WO 2002/35929 A1, the contents of which are incorporated in the present specification by reference. Such medical fluid may comprise salts and nutrients as well as serum albumin and for example dextran compounds. In addition, erythrocytes may be added for oxygen supply. Thus, the evaluation fluid is able to support oxygenation and nutrition of the cells.

However, although the evaluation fluid comprises oncotic agents, there is a risk that the organ forms edema.

A hypothesis is that the vascular system of the organ may have lost its vasotonus. The reason may be that the nerves are at least partly denervated and no activation signals are received by the nerve terminals. Consequently, the nerve terminals do not emit noradrenaline into the synaptic cleft.

In addition, the adrenal medulla is no longer connected to the organ. Thus, the organ does not receive adrenaline and noradrenaline. Depletion of noradrenaline may result for example in that the vascular system of the organ loses its vasotonus, and the vascular bed becomes vasodilated. The endothelial cells may be unable to resist outflow of fluid into the interstitial volume, resulting in edema formation and/or organ swelling. Depletion of adrenaline may result in down-regulation of beta adrenergic cardiac receptors (BAR), i.e. a reduction of BAR density, which potentially may result in poor transplant outcome.

Thus, according to an embodiment, adrenaline may be included in the medical fluid in concentrations lower or similar to those normally encountered in the blood. The added adrenaline interacts with beta-receptors to promote for example cardiac output. Adrenaline has numerous other actions in the organs as is well known to the skilled person.

According to another embodiment, noradrenaline may be included in the medical fluid in concentrations sufficient to cause diffusion from the blood to the synaptic cleft and to the receptors present therein, for example alpha-receptors, in order to interact with for example alpha-receptors to cause vasoconstriction for at least partly maintaining vasotonus. Noradrenaline has numerous other actions in the organs as is well known to the skilled person.

However, noradrenaline is normally produced and normally acts at sites different from the vascular system. This fact may be a cause to different results when adding noradrenaline to fluids entered into the vascular system, as reported in the literature.

One mechanism which may decrease the action of the noradrenaline circulating in the vascular system and diffusing to the synaptic cleft, may be the fact that any noradrenaline reaching the synaptic cleft will be rapidly taken up by the NET transporter and be entered into the presynaptic nerve terminal. Thus, the NET transporter will compete with the activation of the effector cell receptors and decrease the action of the noradrenaline present in the vascular system and diffusing to the synaptic cleft. When added to the vascular system, noradrenaline tends to be absorbed or soaked up by the nerve terminals.

The inventor has found that the addition of cocaine together with noradrenaline would permit the use of lower levels of noradrenaline in the vascular system than normally found in the living body, and still obtain the desired effects of at least partly maintained vasotonus. One hypothesis may be that the cocaine acts as NET inhibitor, which is previously known. By blocking the reuptake of the noradrenaline from the synaptic cleft, the NET transporter will no longer compete with the alpha-receptor and the noradrenaline diffusing from the vascular system to the synaptic cleft may cause the desired action and at least partly maintain vasotonus. Other explanations may be relevant in combination.

By the use of lower than normal concentration of noradrenaline, any negative effect of high concentration of noradrenaline in the vascular system can be counteracted.

In addition, it has been found that cocaine may interact with adrenaline for preserving the BAR receptors, and possibly prevent down-regulation of BAR receptors and may have other beneficial effects.

In a further embodiment, the medical fluid may comprise both adrenaline and noradrenaline and in addition cocaine.

In one embodiment, cocaine (benzoylmethyl ecgonine) has been used. Cocaine acts as a NET inhibitor of noradrenaline and dopamine.

Cocaine may also or alternatively act via further mechanisms not known or appreciated today, and may have a beneficial effect for preserving organs after harvesting.

Cocaine analogues may operate in the same way. Analogues may be any analogue as defined above. It is believed that it is the stimulant effect of cocaine that is active. Thus, cocaine analogues mean cocaine analogues with stimulating effect.

Cocaine-analogues with both stimulant and local anesthetic effects are for example: Dimethocaine or larocaine (DMC) ((3-diethylamino-2,2-dimethylpropyl)-4-aminobenzoate); and 3-(p-fluorobenzoyl)tropane ((1R,5S)-(8-methyl-8-azabicyclo[3.2.1]octan-3-yl)-4-fluorobenzoate).

Cocaine-analogues for stimulant effects with local anesthetic effects removed are for example: β-CIT (methyl (1R,2S,3S,5S)-3-(4-iodophenyl)-8-methyl-8-azabicyclo

[3.2.1]octane-2-carboxylate); β-CPPIT (3β-(4'-chlorophenyl)-2β-(3'-phenylisoxazol-5'-yl)tropane); FE-β-CPPIT (N-(2'-fluoroethyl)-3β-(4'-chlorophenyl)-2β-(3'-phenylisoxazol-5'-yl)nortropane); FP-β-CPPIT (N-(3'-fluoropropyl)-3β-(4'-chlorophenyl)-2β-(3'-phenylisoxazol-5'-yl)nortropane); Altropane (methyl (1R,2S,3S,5S)-3-(4-fluorophenyl)-8-[(E)-3-iodoprop-2-enyl]-8-azabicyclo[3.2.1]octane-2-carboxylate); Brasofensine ((E)-1-[(1R,2R,3S,5S)-3-(3,4-dichlorophenyl)-8-methyl-8-azabicyclo[3.2.1]oct-2-yl]-N-methoxymethanimine); CFT (methyl (1R,2S,3S,5S)-3-(4-fluorophenyl)-8-methyl-8-azabicyclo[3.2.1]octane-2-carboxylate); Dichloropane (methyl (1R,2S,3 S,5S)-3-(3,4-dichlorophenyl)-8-azabicyclo[3.2.1]octane-2-carboxylate); Difluoropine (methyl (1 S,2S,3 S,5R)-3-[bis(4-fluorophenyl)methoxy]-8-methyl-8-azabicyclo[3.2.1]-octane-2-carboxylate); Ioflupane ($^{123}$I) (methyl (1R,2S,3S,5S)-3-(4-iodophenyl)-8-(3-fluoropropyl)-8-azabicyclo[3.2.1]octane-2-carboxylate); Nocaine (methyl (3R,4S)-4-(4-chlorophenyl)-1-methylpiperidine-3-carboxylate); Tesofensine ((1R,2R,3 S, 5 S)-3-(3,4-dichlorophenyl)-2-(ethoxymethyl)-8-methyl-8-azabicyclo[3.2.1]octane); Troparil (methyl (1R,2S,3S,5S)-8-methyl-3-phenyl-8-azabicyclo[3.2.1]octane-2-carboxylate); Tropoxane (methyl (1R,2S,3S,5S)-3-(3,4-dichlorophenyl)-8-oxabicyclo[3.2.1]octane-2-carboxylate); (−)-Methyl-1-methyl-4β-(2-naphthyl)piperidine-3β-carboxylate (methyl (3S,4S)-1-methyl-4-naphthalen-2-ylpiperidine-3-carboxylate); PIT (2-propanoyl-3-(4-isopropylphenyl)-tropane); PTT (2β-propanoyl-3β-(4-tolyl)-tropane); RTI-121, IPCIT (propan-2-yl (1R,2S,3S)-3-(4-iodophenyl)-8-methyl-8-azabicyclo[3.2.1]octane-2-carboxylate); RTI-126 ((1R,2S,3S,5S)-8-methyl-2-(1,2,4-oxadiazol-5-methyl)-3-phenyl-8-azabicyclo[3.2.1]octane); RTI-150 (cyclobutyl (1R,2S,3S,5S)-8-methyl-3-(4-methylphenyl)-8-azabicyclo[3.2.1]octane-2-carboxylate); RTI-336 ((1R,2S,3S,5S)-8-methyl-2-(3-(4-methylphenyl)isoxazol-5-yl)-3-(4-chlorophenyl)-8-azabicyclo[3.2.1]octane); WF-23 (2β-propanoyl-3β-(2-naphthyl)-tropane); WF-33 (2α-(propanoyl)-3β-(2-(6-methoxynaphthyl))-tropane).

The medical fluid according to embodiments may be used for any organ, tissue or part thereof and will have beneficial effects, for example reduced edema formation.

In particular, the heart will benefit by the medical fluid, which in addition seems to decrease cardiac irritability.

In addition, it has been found that pulmonary edema may decrease by the use of the medical fluid, which will improve the result of subsequent pulmonary transplantation.

The same is true for other organs, such as kidney, liver, pancreas, small bowels, intestines, etc. This may be explained by the improved vasotonus obtained.

The medical fluid may in addition to cocaine or a stimulating analogue thereof, adrenaline and/or noradrenaline, further contain additional components such as at least one of: an oncotic agent, such as dextran; hormones, such as thyroxin (T4), triiodotyronine (T3), cortisone; electrolytes and optionally nutrients in substantially physiological concentrations in a physiologically acceptable medium; albumin; and an oxygen carrier, such as erythrocytes; further hormones or substances, such as insulin; dopamine; hydrocortisone; methylprednisolone; and a vasopressor agent, such as desmopressin, or Minirin.

The oncotic agent may be Dextran 40 in a concentration of 0% to 6.0%. Albumin also acts as an oncotic agent and if albumin is present, Dextran 40 may be reduced or eliminated. If no albumin is present, the concentration of Dextran 40 should be in the higher range. Albumin may be replaced by recombinant serum albumin or bovine serum albumin.

Dextran 40 may be partly or entirely replace by Dextran 70 or another Dextran compound and/or derivatives thereof.

The ratio between the cocaine:adrenaline:noradrenaline may be about 1:1:1.

In some embodiments, the adrenaline and/or noradrenaline may be partly or entirely replaced by an equivalent substance. For example, phenylephrine is an alpha-1-agonist and may replace noradrenaline. It seems that phenylephrine is about 5 times less potent as noradrenaline.

Erythrocytes may be replaced by synthetic oxygen carriers.

Dopamine may be added in quantities corresponding to an infusion of less than about 0.01 mg/kg/min.

Hormones should be added as required. It has been found that the levels of the hormones thyroxin (T4), triiodotyronine (T3), and cortisone are reduced rapidly in the harvested organ, and may be replaced and included in the medical fluid. Further hormones may be added as needed, such as insulin. Vasopressin may also be rapidly reduced in the harvested organ and may be included in the medical fluid, for example Desmopressin or Minirin.

Electrolytes and optionally nutrients are included in the medical fluid. Electrolytes are for example those included in Kreb's solution. Nutrients may be physiologically acceptable carbohydrates, such as glucose, fatty acids and amino acids or any combinations thereof.

Further substances may be added, such as antibiotics.

In one embodiment, the medical fluid comprises cocaine or a stimulating analogue, and in addition adrenaline, noradrenaline, cortisone, thyroxin, triiodotyronine, desmopressin, electrolytes and albumin. Erythrocytes are added before use.

The embodiments also relate to a medical fluid comprising the composition as defined above dissolved in a pharmaceutical acceptable medium. Examples of acceptable mediums are physiological sodium chloride solution, Hartmann's solution and Ringer's (acetate) solution or sterile, non-ionic water, i.e. pure $H_2O$.

One embodiment of the medical fluid may have the following composition:

1) The basis is a Kreb's solution, comprising for example NaCl, 110-135 mM; $NaHCO_3$, 15-35 mM; KCl, 2.5-4.6 mM; $MgCl_2$, 1.0-2.6 mM; $CaCl_2$, 1.5-2.4; $NaH_2PO_4$, 1.0-2.0 mM; Glucose 1-15%, such as about 10%. KCl may be 15-25 mM or as high as 125 mM if a cardioplegic fluid is required.

2) Albumin, between 2.0% and 5.5%, such as 5.0%, or between 2.0% and 4.5%, such as 4.0%.

3) Dextran 40, between 0% and 5.0%, such as 0.5%.

4) Cocaine and adrenaline and noradrenaline, each about 0.001 to 0.1 μM, such as 0.01 μM. In another embodiment, cocaine and noradrenaline are included in the mentioned concentrations. In a further embodiment, cocaine and adrenaline are included in the mentioned concentrations.

5) T3/T4, vasopressin and cortisone, each 0.1 μM.

6) Erythrocytes to a hematocrit of 0% to 25%, such as 15%.

Erythrocytes may be replaced by synthetic oxygen carriers.

Dextran 40 may be partly or entirely replace by Dextran 70 or another Dextran compound and/or derivatives thereof.

When the organ has been evaluated by any known method and using the medical fluid, the organ may be preserved awaiting transplantation. Such preservation often takes place in a hypothermic condition, such as a temperature below 20° C., for example below 15° C., such as about 10° C. During hypothermic conditions, the metabolism of the cells of the organ is reduced.

Thus, a preservation fluid may not require all components of the medical fluid.

One embodiment of the medical fluid may have the same composition as the above-mentioned fluid, except:

2) No albumin is required.
3) Dextran 40, between 1% and 5.0%, such as 4%.
6) No erythrocytes are required.

Because the preservation fluid does not comprise albumin and erythrocytes, it is less expensive, but will still maintain the organ in a good condition for subsequent transplantation. The Dextran concentration will be sufficient for maintaining an oncotic pressure, which will prevent edema formation, in addition to cocaine/adrenaline/noradrenaline.

The medical fluid may be provided without erythrocytes, which are added shortly before use.

The medical fluid may be provided without an oncotic agent, which is added shortly before use, such as a combination of albumin and Dextran 40.

Thus, a medical fluid may be provided, which is suitable for preservation. If the solution should be used for evaluation, certain additions are made before use, such as addition of albumin, Dextran 40 and erythrocytes.

The evaluation and preservation may take place by arranging the organ in a device, such as the device disclosed in WO2009136838A1, the contents of which are incorporated in the present specification by reference.

The organ may be partly or completely immersed in the fluid. In addition or alternatively, the fluid may be introduced into the vascular system of the organ and be circulated there through.

Since the evaluation may take place at a physiological temperature, hormones and other substances may be consumed, and need to be replaced intermittently or continuously to maintain the concentration thereof. During hypothermic preservation, replacement may not be required.

During preservation, the circulation may not be required, but the preservation fluid may be present inside the vascular system. In addition or alternatively, the organ may be partly or completely immersed in the preservation fluid.

Instead of immersing the organ in the second fluid, the fluid may be arranged to drip onto the organ, which is surrounded by cloths, so that the organ is kept moist. In addition, the organ may be arranged in a moist atmosphere.

There is no strict distinction between a preservation fluid and an evaluation fluid. Thus, the same medical fluid may be used for evaluation and preservation purposes.

Another alternative option is to use a more versatile first medical fluid inside the vascular system and a less versatile second medical fluid outside the organ, which is partly or completely immersed in the second fluid. In this case the first fluid may comprise erythrocytes and/or albumin, while the second fluid may lack erythrocytes and/or albumin.

In addition, the evaluation at the same time comprises preservation, since the evaluation takes some time during which the organ needs to be preserved.

As mentioned above, there are indications in the literature that a noradrenaline plasma concentration in the living body of about 1.5 mg per liter (about 9 µM) is required in order to observe a physiological change. Furthermore, the addition of noradrenaline in such concentration has been reported to have adverse effects. Thus, addition of noradrenaline in a concentration below 0.1 µM should be expected to have substantially no effect. However, the inclusion of cocaine seems to potentiate the effect of noradrenaline so that a favorable effect is obtained, without causing adverse effects. Without being bound by any theory, the above explanation may be valid.

The corresponding plasma concentration for adrenaline is about 0.05 mg per liter (0.3 µM). Also for adrenaline, the cocaine seems to have a potentiating effect so that low concentrations of adrenaline still results in a favorable effect.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a," "an," "first," "second," etc., do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. A method for preservation and/or evaluation of a harvested organ comprising:
   circulating a medical fluid in the vascular system of the harvested organ, wherein:
   the medical fluid comprises: cocaine or a cocaine analogue with stimulating effect; adrenaline; and noradrenaline; and
   the harvested organ is at least partly denervated,
   wherein the cocaine or the cocaine analogue is present in the medical fluid at a concentration of 0.010 µM to 0.100 µM.

2. The method according to claim 1, wherein the medical fluid further comprises: an oncotic agent; and electrolytes in physiological concentrations in a physiologically acceptable medium.

3. The method according to claim 1, wherein the adrenaline and the noradrenaline are present in the medical fluid at concentrations that are subphysiological.

4. The method according to claim 1, wherein:
   the adrenaline is present in the medical fluid at a concentration of 0.010 µM to 0.100 µM; and
   the noradrenaline is present in the medical fluid at a concentration of 0.010 µM to 0.100 µM.

5. The method according to claim 1, wherein the cocaine or the cocaine analogue, the adrenaline, and the noradrenaline are present in the medical fluid at concentrations that are equimolar.

6. The method according to claim 1, wherein the harvested organ comprises a lung, lungs, or a heart.

7. The method according to claim 1, wherein:
   the medical fluid further comprises: an oncotic agent; and electrolytes in physiological concentrations in a physiologically acceptable medium; and
   the adrenaline and the noradrenaline are present in the medical fluid at concentrations that are subphysiological.

8. The method according to claim 1, wherein:
   the medical fluid further comprises: an oncotic agent; and electrolytes in physiological concentrations in a physiologically acceptable medium;

the adrenaline is present in the medical fluid at a concentration of 0.010 µM to 0.100 µM; and the noradrenaline is present in the medical fluid at a concentration of 0.010 µM to 0.100 µM.

9. The method according to claim 8, wherein the harvested organ comprises a lung, lungs, or a heart.

10. The method according to claim 1, wherein:

the medical fluid further comprises: an oncotic agent; and electrolytes in physiological concentrations in a physiologically acceptable medium; and the cocaine or the cocaine analogue, the adrenaline, and the noradrenaline are present in the medical fluid at concentrations that are equimolar.

11. The method according to claim 1, wherein the medical fluid comprises the cocaine.

12. The method according to claim 11, wherein the medical fluid further comprises: an oncotic agent; and electrolytes in physiological concentrations in a physiologically acceptable medium.

13. The method according to claim 11, wherein the adrenaline and the noradrenaline are present in the medical fluid at concentrations that are subphysiological.

14. The method according to claim 11, wherein:

the adrenaline is present in the medical fluid at a concentration of 0.010 µM to 0.100 µM; and the noradrenaline is present in the medical fluid at a concentration of 0.010 µM to 0.100 µM.

15. The method according to claim 11, wherein the cocaine, the adrenaline, and the noradrenaline are present in the medical fluid at concentrations that are equimolar.

16. The method according to claim 11, wherein the harvested organ comprises a lung, lungs, or a heart.

* * * * *